(12) United States Patent
Yonehara

(10) Patent No.: US 6,177,268 B1
(45) Date of Patent: Jan. 23, 2001

(54) METHOD FOR STABILIZING TRYPSIN, METHOD FOR INCREASING ENZYMATIC ACTIVITY OF TRYPSIN, AND KIT FOR MEASURING ENZYMATIC ACTIVITY OF TRYPSIN

(75) Inventor: Satoshi Yonehara, Osaka (JP)

(73) Assignee: Arkray, Inc., Kyoto (JP)

( * ) Notice: Under 35 U.S.C. 154(b), the term of this patent shall be extended for 0 days.

(21) Appl. No.: 09/203,195

(22) Filed: Nov. 30, 1998

(30) Foreign Application Priority Data

Dec. 5, 1997 (JP) .................................................. 9-336160

(51) Int. Cl.[7] .............................. C12N 9/96; C12N 9/76; C12Q 1/37; A61K 38/48
(52) U.S. Cl. ........................... 435/188; 435/213; 435/23; 424/94.3; 424/94.64
(58) Field of Search .................................... 435/188, 213, 435/23; 560/19; 424/94.64, 94.3

(56) References Cited

U.S. PATENT DOCUMENTS

| | | | |
|---|---|---|---|
| 3,928,305 | 12/1975 | Werle et al. | 260/112.5 |
| 3,959,080 | 5/1976 | Orth et al. | 195/63 |
| 4,918,016 | 4/1990 | Leuba et al. | 435/176 |
| 4,973,554 | 11/1990 | Luong et al. | 435/213 |

OTHER PUBLICATIONS

Walsh et al. Serine Proteases, Methods in Enzymology, 19, pp. 31–63. (1970). No month found.

Vajda et al. Comparison of the effect of calcium (II) and manganese (II) ions on trypsin autolysis. J. Inorganic Biochemistry, 15 (4), pp. 307–315. (1981). No month found.

SIGMA chemical company catalog, p. 1026. (1994). No month found.

*Primary Examiner*—M P Woodward
*Assistant Examiner*—Marjorie A. Moran
(74) *Attorney, Agent, or Firm*—Merchant & Gould P.C.

(57) ABSTRACT

The present invention provides a method for stabilizing trypsin, in which enzyme reaction of trypsin can be generated in a two-solution system, degradation of trypsin and its substrate can be prevented, and enzymatic activity of trypsin is improved compared to conventional methods, and which can be sufficiently applied to an automatic analyzer. An enzyme solution is prepared by dissolving trypsin in a buffer solution having a pH at which enzymatic activity of trypsin is active and containing calcium and/or manganese ions. It is preferable that the total concentration of the calcium ions and the manganese ions in the buffer solution is in the range of 3 to 10 mmol/l. It is also preferable that the concentration of the buffer solution is at least 10 mmol/l, and that the pKa of the buffer solution is higher than the pH of the buffer solution.

19 Claims, No Drawings

METHOD FOR STABILIZING TRYPSIN, METHOD FOR INCREASING ENZYMATIC ACTIVITY OF TRYPSIN, AND KIT FOR MEASURING ENZYMATIC ACTIVITY OF TRYPSIN

FIELD OF THE INVENTION

The present invention relates to a method for stabilizing trypsin in which autolysis of trypsin is inhibited, a method for increasing enzymatic activity of trypsin, and to a kit for measuring enzymatic activity of trypsin.

BACKGROUND OF THE INVENTION

When measuring enzymatic activity of trypsin, generally an aqueous solution of trypsin (an enzyme solution), a buffer solution, and a substrate solution are prepared separately, and these three solutions are admixed so as to generate enzyme reaction. When trypsin is dissolved and stored in a purified water, the amount of trypsin often decreases due to autolysis. In order to prevent this phenomenon, the pH of an aqueous trypsin solution is usually adjusted to a range in which the trypsin is inactive but not deactivated. For example, trypsin may be dissolved in a hydrochloric acid aqueous solution (1 mmol/l). Also, in order to further increase the stability of trypsin, calcium ions may be added to the hydrochloric acid aqueous solution.

However, in the above-mentioned conventional method of mixing three solutions, additional labor is required for preparing the solutions and for measuring the enzyme reaction. Furthermore, when measuring the enzymatic activity of trypsin with an automatic analyzer in a clinical test or the like, which requires processing a large amount of sample, it is desired to integrate such a three-solution system into a two-solution system. Therefore, dissolving a substrate in a buffer solution may be considered, but there is a problem that α-benzoyl-arginine-p-nitroanilide (BAPNA) or the like generally used as a synthetic substrate for trypsin is unstable in a buffer solution.

Furthermore, in the above-mentioned automatic analyzer or the like, it is desired to prepare a dry reagent by drying a reagent used for measuring the enzymatic activity of trypsin, and adhering it to a test piece or the like. However, when trypsin is stabilized using hydrochloric acid as mentioned above, the hydrochloric acid volatilizes during the drying step, so that the stability of trypsin is reduced. Although other non-volatile acids may be used in place of hydrochloric acid, there is a possibility that acid concentration is increased in the drying step, resulting in deactivation of trypsin, if such acids are used.

SUMMARY OF THE INVENTION

Accordingly, in order to solve these problems, a new method for stabilizing trypsin, which is different from conventional methods is desired. Furthermore, in a clinical test or the like utilizing enzyme reaction of trypsin, it is desirable to increase the enzymatic activity of trypsin so as to improve test precision, processing speed, and the like. Furthermore, in order to improve efficiency of such a clinical test, an improved kit for measuring the enzymatic activity of trypsin is also desired.

It is a first object of the present invention to provide a method for stabilizing trypsin, in which degradation of trypsin can be prevented, and to provide a stabilized trypsin solution which can be applied to an automatic analyzer. It is further a second object of the present invention to provide a method for increasing the enzymatic activity of trypsin. It is still further a third object of the present invention to provide a kit for measuring enzymatic activity of trypsin, in which enzyme reaction of trypsin can be generated in a two-solution system and degradation of trypsin and its substrate is prevented.

In order to achieve the above-mentioned first and second objects, the present invention provides a method for stabilizing trypsin prior to enzyme reaction or for increasing the enzymatic activity of trypsin, which comprises dissolving trypsin in a buffer solution having a pH at which trypsin is active and containing calcium and/or manganese ions.

Accordingly, in the present invention, trypsin is dissolved in a buffer solution having a pH at which trypsin is active, together with calcium ions or the like as enzymatic activity accelerators. This is contrary to traditional thought. It has been considered that, in such a buffer solution, trypsin attacks against one another causing autolysis, so that the concentration of trypsin is decreased, thus having an adverse effect on stabilization.

Therefore, trypsin has been stored by dissolving it in a hydrochloric acid aqueous solution having a pH range at which it is inactive, while calcium ions as enzymatic activity accelerators have been dissolved in a buffer solution (with a pH at which trypsin is active). However, as a result of elaborate studies and experiments with regard to these conventional conditions for enzyme reaction of trypsin, the inventor of the present invention have found out that, surprisingly, trypsin can be stored in a highly stable condition without causing autolysis, if the trypsin is dissolved in a buffer solution together with calcium ions or the like. Therefore, by employing this method for stabilizing trypsin, it is possible to generate enzyme reaction of trypsin in a two-solution system comprising a buffer solution in which trypsin is dissolved together with calcium ions or the like, and a substrate solution. Accordingly, labor which has been required for preparing for enzyme reaction and for measuring the reaction can be reduced, and also stability of the substrate can be ensured. Furthermore, this method can be applied to an automatic analyzer as well as to drying of reagents, etc.

Furthermore, according to the method of the present invention, enzymatic activity of trypsin can be increased compared to conventional methods.

In the method for stabilizing trypsin or for increasing enzymatic activity of trypsin according to the present invention, the total concentration of calcium ions and manganese ions in the buffer solution is preferably in the range of 1 to 200 mmol/l, particularly preferably 3 to 10 mmol/l. Furthermore, in the case of using calcium ions only, the concentration thereof in the buffer solution is preferably 1 to 200 mmol/l; and in the case of using manganese ions only, the concentration thereof in the buffer solution is preferably 1 to 200 mmol/l. Although there is no difference between calcium ions and manganese ions with respect to the stability of trypsin, because calcium ions are stronger than manganese ions as enzymatic activity accelerators, calcium ions are preferably used. It is also possible to use both of these ions together.

In the method for stabilizing trypsin according to the present invention, the concentration of the buffer solution is preferably at least 10 mmol/l, particularly preferably in the range of 50 to 500 mmol/l.

In the method for stabilizing trypsin according to the present invention, it is preferable that the pKa of the buffer solution is higher than the pH of the buffer solution.

Next, in order to achieve the above-mentioned third object, the present invention provides a kit for measuring enzymatic activity of trypsin, which comprises a trypsin solution in which trypsin is dissolved in a buffer solution having a pH at which trypsin is active and containing at least calcium and/or manganese ions.

In the kit according to the present invention, it is preferable that the kit further comprises a substrate for trypsin as well as the trypsin solution.

In the kit according to the present invention, as in above-mentioned method for stabilizing trypsin, the total concentration of calcium ions and manganese ions in the buffer solution is preferably in the range of 1 to 200 mmol/l, particularly preferably 3 to 10 mmol/l. Furthermore, in the case of using calcium ions only, the concentration thereof in the buffer solution is preferably 1 to 200 mmol/l; and in the case of using manganese ions only, the concentration thereof in the buffer solution is preferably 1 to 200 mmol/l. Although there is no difference between calcium ions and manganese ions with respect to the stability of trypsin, because calcium ions are better enzymatic activity accelerators, calcium ions are preferably used. It is also possible to use both of these ions together.

In the kit according to the present invention, as in the above-mentioned method for stabilizing trypsin, the concentration of the buffer solution is preferably at least 10 mmol/l, particularly preferably 50 to 500 mmol/l.

In the kit according to the present invention, as in the above-mentioned method for stabilizing trypsin, it is preferable that the pKa of the buffer solution is higher than the pH of the buffer solution.

The kit according to the present invention preferably has a two-solution system comprising the above-mentioned trypsin solution and a substrate solution, but it may also further comprise other reagent solutions. Examples of such other reagent solutions include surfactants, water-soluble polymers, and the like.

In the present invention, the type of the buffer solution used is not particularly limited, and examples include glycylglycine buffer, tris buffer, N-tris(hydroxymethyl)-methyl-2-aminoethanesulfonic acid (TES) buffer, N-(2-acetamido) iminodiacetic acid (ADA) buffer, triethanolamine (TEA) buffer, imidazole buffer, glycine buffer, 2-[4-(2-hydroxyethyl)-1-piperazinyl]ethanesulfonic acid (HEPES) buffer, and the like. The pH of the buffer solution is usually in the range of pH 5 to 10, preferably pH 6.5 to 8.5. Furthermore, the buffer solution may also contain other components such as surfactants, water-soluble polymers, and the like.

In the present invention, the type of the substrate used is not particularly limited, and examples include BAPNA, Nα-p-tosyl-L-arginine methyl ester (TAME), Nα-p-benzoyl-L-arginine ethyl ester (BAEE), and the like, preferably L-BAPNA and BAEE. Furthermore, the concentration of the substrate in the enzyme reaction solution is not particularly limited, as long as it is soluble, but it is usually at least 0.1 mmol/l, preferably 1 to 10 mmol/l. The substrate solution may also contain other components, e.g. a surfactant.

In the present invention, the type of trypsin is not particularly limited, and for example, trypsin derived from bovine pancreas or from swine pancreas may be used.

Furthermore, the present invention provides a stabilized trypsin solution. The stabilized trypsin solution is obtainable by the above-mentioned method according to the present invention. The stabilized trypsin solution comprises trypsin, a buffer solution and calcium and/or manganese ions, wherein the buffer solution has a pH at which trypsin is active.

Furthermore, the present invention provides a method of preparing a reagent for use in measuring the enzymatic activity of trypsin, said method comprising the step of drying the stabilized trypsin solution.

The application range of the present invention is not particularly limited, as long as it is a field in which generation of enzyme reaction of trypsin is required. Examples of such a field include food industry, detergents, tests for clinical medicine, biochemistry, and the like. Furthermore, it may also be applied to such a field as measuring urinary trypsin inhibitor (UTI), and the like.

DETAILED DESCRIPTION OF THE INVENTION

The present invention will be described in detail referring to Examples and Comparative Examples as follow.

EXAMPLE 1, COMPARATIVE EXAMPLE 1

The reagent solutions used are shown as follows:

| | |
|---|---|
| HCl solution | 0.001 mol/l |
| Gg1 buffer solution (Glycylglycine is dissolved only.) | 0.010 mol/l |
| Gg2 buffer solution (Glycylglycine is dissolved; and pH is adjusted to 7.5.) | 0.010 mol/l |
| Gg3 buffer solution (Glycylglycine is dissolved; and pH is adjusted to 7.5.) | 0.100 mol/l |
| Surfactant solution (Triton X 405, produced by Nacalai tesque Inc.) | 10 weight % |
| Trypsin solution (trypsin: produced by Sigma Chemical Co.) | 16,400 U/mg (1.0 g/l) |
| CaCl$_2$ solution | 0.4 mol/l |
| MnCl$_2$ solution | 0.4 mol/l |

First, 1.0 g of the trypsin solution was added to 30 g of the HCl solution, the Gg1 buffer solution, the Gg2 buffer solution and the Gg3 buffer solution, respectively, to prepare four types of basic solutions. Then, according to the compositions A, B and C as shown in Table 1 below, ten types of enzyme solutions ((a) to (j)) shown below were prepared by combining the four basic solutions with the CaCl$_2$ solution, the MnCl$_2$ solution, and distilled water (D.W.). In these enzyme solutions, the compositions B and C are for Example 1 of the present invention, and the composition A is for Comparative Example 1.

TABLE 1

| | Composition | | |
|---|---|---|---|
| | A | B | C |
| Basic Solution | 1.2 ml | 1.2 ml | 1.2 ml |
| CaCl$_2$ | | 0.10 ml | |
| MnCl$_2$ | | | 0.10 ml |
| D.W. | 0.10 ml | | |

Type of Enzyme
Composition A: (Comparative Example 1)
(a) HCl 1 mmol/l
(b) Gg1 buffer solution
(e) Gg2 buffer solution
(h) Gg3 buffer solution Composition B: (Example 1)
  (c) Gg1 buffer solution, containing CaCl$_2$
  (f) Gg2 buffer solution, containing CaCl$_2$
  (i) Gg3 buffer solution, containing CaCl$_2$
Composition C: (Example 1)
  (d) Gg1 buffer solution, containing MnCl$_2$
  (g) Gg2 buffer solution, containing MnCl$_2$
  (j) Gg3 buffer solution, containing MnCl$_2$ Next, these enzyme solutions (a) to (j) were respectively put into 6 ml capacity glass bottles, and stored at each temperature of 10° C., 25° C. and 40° C.

On the other hand, a substrate solution was prepared by dissolving L-BAPNA in a buffer solution having the composition below in the proportion of 1.305 g/kg (buffer solution).

Buffer Solution Composition

| | |
|---|---|
| Glycylglycine | 0.1 mol/l |
| CaCl$_2$ | 10 mmol/l |
| Surfactant (Triton X 405, produced by Nacalai tesque Inc.) | 0.04 weight % |

Then, the above-mentioned enzyme solutions ((a) to (j)), which had been stored for given periods, were mixed with the above-mentioned substrate solution, and the enzyme reaction was measured. This measurement was carried out by measuring absorbance with an automatic analyzer for clinical tests (COBAS-MIRA, produced by Nippon Roche Ltd.). The results are shown in Table 2-1, Table 2-2, Table 3-1 and Table 3-2 below.

In the measurement of absorbance as mentioned above, a blank was prepared by mixing distilled water with the substrate solution. Table 2-1 and Table 2-2 show the values obtained by subtracting the measured blank values from the observed values (blank correction value), and Table 3-1 and Table 3-2 show relative values (%), using as a standard (100%) the blank correction value when each enzyme solution was stored at 10° C. for 24 hours.

TABLE 2-1

Blank Correction Value

| | | Enzyme Solution | | | | |
|---|---|---|---|---|---|---|
| Storage Period | | (a) | (b) | (c) | (d) | (e) |
| (10° C.) | 24 h | 0.166 | 0.092 | 0.163 | 0.154 | 0.125 |
| | 44 h | 0.156 | 0.088 | 0.156 | 0.153 | 0.112 |
| | 68 h | 0.150 | 0.080 | 0.153 | 0.149 | 0.107 |
| | 116 h | 0.152 | 0.073 | 0.152 | 0.147 | 0.092 |
| | 284 h | 0.151 | 0.068 | 0.151 | 0.146 | 0.070 |
| | 452 h | 0.150 | 0.062 | 0.156 | 0.149 | 0.054 |
| | 716 h | 0.149 | 0.037 | 0.148 | 0.143 | 0.028 |
| (25° C.) | 24 h | 0.158 | 0.072 | 0.158 | 0.152 | 0.058 |
| | 44 h | 0.153 | 0.058 | 0.150 | 0.143 | 0.034 |
| | 68 h | 0.153 | 0.038 | 0.146 | 0.143 | 0.013 |
| | 284 h | 0.100 | 0.000 | 0.136 | 0.138 | 0.000 |
| (40° C.) | 24 h | 0.147 | 0.007 | 0.158 | 0.156 | 0.000 |
| | 44 h | 0.135 | 0.000 | 0.146 | 0.145 | 0.000 |
| | 68 h | 0.134 | | 0.144 | 0.144 | |
| | 116 h | 0.103 | | 0.134 | 0.134 | |
| | 284 h | 0.024 | | 0.121 | 0.122 | |
| | 452 h | 0.070 | | 0.121 | 0.117 | |
| | 716 h | 0.000 | | 0.098 | 0.106 | |

TABLE 2-2

Blank Correction Value

| | | Enzyme Solution | | | | |
|---|---|---|---|---|---|---|
| Storage Period | | (f) | (g) | (h) | (i) | (j) |
| (10° C.) | 24 h | 0.207 | 0.203 | 0.133 | 0.160 | 0.154 |
| | 44 h | 0.203 | 0.198 | 0.138 | 0.157 | 0.154 |
| | 68 h | 0.201 | 0.194 | 0.132 | 0.152 | 0.153 |
| | 116 h | 0.198 | 0.194 | 0.128 | 0.155 | 0.145 |
| | 284 h | 0.197 | 0.192 | 0.123 | 0.151 | 0.148 |
| | 452 h | 0.202 | 0.194 | 0.118 | 0.159 | 0.147 |
| | 716 h | 0.196 | 0.187 | 0.118 | 0.156 | 0.149 |
| (25° C.) | 24 h | 0.205 | 0.199 | 0.125 | 0.159 | 0.154 |
| | 44 h | 0.197 | 0.190 | 0.117 | 0.152 | 0.146 |
| | 68 h | 0.191 | 0.186 | 0.105 | 0.147 | 0.147 |
| | 284 h | 0.181 | 0.183 | 0.081 | 0.147 | 0.144 |
| (40° C.) | 24 h | 0.197 | 0.197 | 0.049 | 0.156 | 0.152 |
| | 44 h | 0.189 | 0.188 | 0.031 | 0.150 | 0.135 |
| | 68 h | 0.182 | 0.174 | 0.022 | 0.147 | o.i45 |
| | 116 h | 0.166 | 0.160 | 0.007 | 0.142 | 0.137 |
| | 284 h | 0.146 | 0.138 | 0.000 | 0.132 | 0.127 |
| | 452 h | 0.128 | 0.121 | | 0.132 | 0.122 |
| | 716 h | 0.105 | 0.103 | | 0.116 | 0.106 |

TABLE 3-1

Relative Value

| | | Enzyme Solution | | | |
|---|---|---|---|---|---|
| Storage Period | | (a) | (b) | (c) | (d) |
| (10° C.) | 24 h | 100.0 | 100.0 | 100.0 | 100.0 |
| | 44 h | 94.4 | 95.3 | 95.3 | 99.6 |
| | 68 h | 90.7 | 87.0 | 93.7 | 97.2 |
| | 116 h | 91.8 | 79.1 | 93.3 | 95.7 |
| | 284 h | 91.3 | 73.6 | 92.4 | 94.8 |
| | 452 h | 90.5 | 66.8 | 95.7 | 97.0 |
| | 716 h | 90.1 | 40.1 | 90.6 | 93.1 |
| (25° C.) | 24 h | 95.6 | 78.3 | 96.7 | 98.7 |
| | 44 h | 92.4 | 62.5 | 91.8 | 93.3 |
| | 68 h | 92.6 | 40.8 | 89.4 | 93.1 |
| | 284 h | 60.2 | 0.0 | 83.3 | 89.8 |
| (40° C.) | 24 h | 88.5 | 7.6 | 96.9 | 101.3 |
| | 44 h | 81.7 | 0.0 | 89.6 | 94.6 |
| | 68 h | 80.7 | | 88.2 | 93.7 |
| | 116 h | 62.0 | | 82.2 | 87.2 |
| | 284 h | 14.7 | | 74.3 | 79.2 |
| | 452 h | 42.1 | | 74.3 | 76.4 |
| | 716 h | 0.2 | | 60.2 | 69.0 |

TABLE 3-2

Relative Value

| | | Enzyme Solution | | | | | |
|---|---|---|---|---|---|---|---|
| Storage Period | | (e) | (f) | (g) | (h) | (i) | (j) |
| (10° C.) | 24 h | 100.0 | 100.0 | 100.0 | 100.0 | 100.0 | 100.0 |
| | 44 h | 89.6 | 97.7 | 97.5 | 104.0 | 98.3 | 99.8 |
| | 68 h | 85.3 | 96.9 | 95.7 | 99.2 | 95.2 | 99.1 |
| | 116 h | 73.9 | 95.7 | 95.9 | 96.5 | 97.1 | 94.2 |
| | 284 h | 56.0 | 95.2 | 94.9 | 92.5 | 94.4 | 96.1 |
| | 452 h | 43.5 | 97.6 | 95.9 | 88.7 | 99.6 | 95.7 |
| | 716 h | 22.1 | 94.7 | 92.3 | 88.7 | 97.7 | 96.8 |
| (25° C.) | 24 h | 46.4 | 98.9 | 98.2 | 94.2 | 99.6 | 100.0 |
| | 44 h | 27.2 | 95.0 | 93.8 | 88.4 | 95.4 | 95.0 |
| | 68 h | 10.1 | 92.1 | 91.6 | 79.4 | 91.9 | 95.5 |
| | 284 h | 0.0 | 87.5 | 90.5 | 61.3 | 92.3 | 93.5 |

TABLE 3-2-continued

| | Relative Value | | | | | |
|---|---|---|---|---|---|---|
| | Enzyme Solution | | | | | |
| Storage Period | (e) | (f) | (g) | (h) | (i) | (j) |
| (40° C.) 24 h | 0.0 | 94.9 | 97.0 | 36.7 | 97.5 | 98.5 |
| 44 h | 0.0 | 91.3 | 92.9 | 23.6 | 94.2 | 87.9 |
| 68 h | | 87.9 | 85.9 | 16.6 | 91.9 | 94.4 |
| 116 h | | 80.1 | 79.1 | 5.3 | 88.7 | 89.2 |
| 284 h | | 70.6 | 68.1 | 0.0 | 82.5 | 82.7 |
| 452 h | | 61.9 | 59.5 | | 82.9 | 79.2 |
| 716 h | | 50.5 | 51.0 | | 72.4 | 68.8 |

From the results of above Table 2-1, Table 2-2, Table 3-1 and Table 3-2, it was found that, in the enzyme solutions not containing calcium ions nor manganese ions, trypsin was quickly degraded when stored at 25° C. and at 40° C. Furthermore, in the enzyme solutions containing calcium ions or manganese ions, stability of trypsin was higher than in the enzyme solution containing hydrochloric acid, and improvement in the enzymatic activity was observed. Moreover, no difference was observed between calcium ions and manganese ions with respect to an effect of stabilizing trypsin. Also, the higher the buffer concentration (glycylglycine concentration) in the enzyme solution, the better the stability of trypsin, and the lower the buffer concentration in the enzyme solution, the higher the enzymatic activity of trypsin.

EXAMPLE 2, COMPARATIVE EXAMPLE 2

The reagent solutions used are shown as follows:

| | |
|---|---|
| HCl solution | 0.001 mol/l |
| Tris1 buffer solution (Tris-HCl, pH 7.5, pKa 8.06) | 0.01 mol/l |
| Tris2 buffer solution (Tris-HCl, pH 8.5, pKa 8.06) | 0.01 mol/l |
| Tris3 buffer solution (Tris-HCl, pH 7.5, pKa 8.06) | 0.1 mol/l |
| TES buffer solution (pH 7.5, pKa 7.5) | 0.01 mol/l |
| ADA buffer solution (pH 7.0, pKa 6.62) | 0.01 mol/l |
| TEA buffer solution (pH 8.0, pKa 7.76) | 0.01 mol/l |
| Surfactant solution (Triton X 405, produced by Nacalai tesque Inc.) | 10 weight % |
| Trypsin solution (trypsin: produced by Sigma Chemical Co.) | 16,400 U/mg (1.0 g/l) |
| $CaCl_2$ solution | 0.4 mol/l |
| $MnCl_2$ solution | 0.4 mol/l |
| $MgCl_2$ solution | 0.4 mol/l |
| $ZnCl_2$ solution | 0.04 mol/l (0.02 mol/l HCl) |

First, 1.0 g of trypsin solution was added to 30 g of the HCl solution, the Tris1 buffer solution, the Tris2 buffer solution and the Tris3 buffer solution, the TES buffer solution, the ADA buffer solution and the TEA buffer solution, respectively, so as to prepare seven types of basic solutions. Then, according to the compositions A, B, C, D and E as shown in Table 4 below, twenty-one types of enzyme solutions ((a) to (u)) shown below were prepared by combining the seven basic solutions with the $CaCl_2$ solution, the $MnCl_2$ solution, the $MgCl_2$ solution, the $ZnCl_2$ solution and distilled water (D.W.). In these enzyme solutions, the compositions B and C are for Example 2 of the present invention, and the compositions A, D and E are for Comparative Example 2.

TABLE 4

| | Composition | | | | |
|---|---|---|---|---|---|
| | A | B | C | D | E |
| Basic Solution | 3.0 ml | 3.0 ml | 3.0 ml | 3.0 ml | 3.0 ml |
| $CaCl_2$ | | 0.10 ml | | | |
| $MnCl_2$ | | | 0.10 ml | | |
| $MgCl_2$ | | | | 0.10 ml | |
| $ZnCl_2$ | | | | | 0.10 ml |
| D.W. | 0.10 ml | | | | |

Type of Enzyme

Composition A: (Comparative Example 2)
 (a) HCl 1 mmoll
 (b) Tris 1 buffer solution
 (g) Tris2 buffer solution
 (j) Tris3 buffer solution
 (m) TES buffer solution
 (p) ADA buffer solution
 (s) TEA buffer solution Composition B: (Example 2)
 (c) Tris1 buffer solution, containing $CaCl_2$
 (h) Tris2 buffer solution, containing $CaCl_2$
 (k) Tris3 buffer solution, containing $CaCl_2$
 (n) TES buffer solution, containing $CaCl_2$
 (q) ADA buffer solution, containing $CaCl_2$
 (t) TEA buffer solution, containing $CaCl_2$ Composition C: (Example 2)
 (d) Tris1 buffer solution, containing $MnCl_2$
 (i) Tris2 buffer solution, containing $MnCl_2$
 (l) Tris3 buffer solution, containing $MnCl_2$
 (o) TES buffer solution, containing $MnCl_2$
 (r) ADA buffer solution, containing $MnCl_2$
 (u) TEA buffer solution, containing $MnCl_2$ Composition D: (Comparative Example 2)
 (e) Tris1 buffer solution, containing $MgCl_2$ Composition E: (Comparative Example 2)
 (f) Trisl buffer solution, containing $ZnCl_2$ Next, these enzyme solutions (a) to (u) were respectively put into 6 ml capacity glass bottles, and stored at each temperature of 10° C., 25° C. and 40° C.

On the other hand, a substrate solution of L-BAPNA was prepared in the same way as mentioned above.

Then, after storing the above-mentioned enzyme solutions for given periods in the same way as mentioned above, they were mixed with the substrate solution, and the enzyme reaction was measured by measuring absorbance. The results are shown in Table 5-1, Table 5-2, Table 5-3, Table 5-4, Table 6-1, Table 6-2, Table 6-3 and Table 6-4 below.

In the measurement of absorbance mentioned above, a blank (0) was prepared by mixing distilled water with the substrate solution. Table 5-1, Table 5-2, Table 5-3 and Table 5-4 above show the values obtained by subtracting the measured blank values from the observed values (blank correction values), and Table 6-1 and Table 6-2, Table 6-3 and Table 6-4 show relative values (%), using as a standard (100%) the blank correction value when each enzyme solution was stored at 10° C. for 20 hours.

TABLE 5-1

Black Correction Value

| Storage Period | Blank (0) | Enzyme Solution (a) | (b) | (c) | (d) | (e) | (f) |
|---|---|---|---|---|---|---|---|
| (10° C.) 20 h | 0.000 | 0.155 | 0.086 | 0.168 | 0.160 | 0.154 | 0.092 |
| 44 h | 0.000 | 0.151 | 0.079 | 0.160 | 0.151 | 0.153 | 0.075 |
| 116 h | 0.000 | 0.148 | 0.067 | 0.162 | 0.148 | 0.144 | 0.070 |
| 332 h | 0.000 | 0.150 | 0.036 | 0.156 | 0.147 | 0.140 | 0.043 |
| 524 h | 0.000 | 0.145 | 0.024 | 0.154 | 0.145 | 0.138 | 0.040 |
| (25° C.) 20 h | | 0.158 | 0.032 | 0.162 | 0.154 | 0.140 | 0.055 |
| 44 h | | 0.151 | 0.012 | 0.153 | 0.154 | 0.134 | 0.037 |
| 116 h | | 0.141 | 0.003 | 0.156 | 0.146 | 0.113 | 0.015 |
| 332 h | | 0.120 | 0.000 | 0.144 | 0.132 | 0.071 | 0.005 |
| (40° C.) 20 h | | 0.150 | 0.000 | 0.156 | 0.148 | 0.057 | 0.006 |
| 44 h | | 0.141 | 0.000 | 0.146 | 0.140 | 0.035 | 0.002 |
| 116 h | | 0.122 | | 0.130 | 0.122 | 0.015 | 0.000 |
| 332 h | | 0.089 | | 0.098 | 0.088 | 0.005 | 0.000 |
| 524 h | | 0.023 | | 0.080 | 0.070 | | |

TABLE 5-2

Blank Correction Value

| Storage Period | Enzyme Solution (g) | (h) | (i) | (j) | (k) | (l) |
|---|---|---|---|---|---|---|
| (10° C.) 20 h | 0.061 | 0.175 | 0.163 | 0.164 | 0.180 | 0.173 |
| 44 h | 0.046 | 0.171 | 0.158 | 0.162 | 0.177 | 0.166 |
| 116 h | 0.026 | 0.168 | 0.154 | 0.160 | 0.177 | 0.170 |
| 332 h | 0.009 | 0.163 | 0.122 | 0.143 | 0.174 | 0.167 |
| 524 h | 0.006 | 0.159 | 0.097 | 0.136 | 0.172 | 0.095 |
| (25° C.) 20 h | 0.010 | 0.166 | 0.160 | 0.141 | 0.177 | 0.167 |
| 44 h | 0.003 | 0.163 | 0.154 | 0.123 | 0.175 | 0.164 |
| 116 h | 0.001 | 0.158 | 0.119 | 0.088 | 0.170 | 0.163 |
| 332 h | 0.000 | 0.149 | 0.043 | 0.045 | 0.158 | 0.112 |
| (40° C.) 20 h | 0.000 | 0.151 | 0.135 | 0.024 | 0.166 | 0.157 |
| 44 h | 0.000 | 0.134 | 0.111 | 0.013 | 0.153 | 0.143 |
| 116 h | | 0.098 | 0.037 | 0.004 | 0.126 | 0.105 |
| 332 h | | 0.052 | 0.001 | 0.002 | 0.076 | 0.019 |
| 524 h | | 0.036 | | | 0.056 | 0.013 |

TABLE 5-3

Blank Correction Value

| Storage Period | Enzyme Solution (m) | (n) | (o) | (p) | (q) | (r) |
|---|---|---|---|---|---|---|
| (10° C.) 20 h | 0.093 | 0.171 | 0.161 | 0.115 | 0.155 | 0.140 |
| 44 h | 0.088 | 0.165 | 0.158 | 0.107 | 0.153 | 0.139 |
| 116 h | 0.073 | 0.164 | 0.155 | 0.088 | 0.148 | 0.124 |
| 332 h | 0.051 | 0.162 | 0.155 | 0.068 | 0.147 | 0.137 |
| 524 h | 0.035 | 0.157 | 0.152 | 0.061 | 0.142 | 0.133 |
| (25° C.) 20 h | 0.050 | 0.167 | 0.157 | 0.070 | 0.150 | 0.133 |
| 44 h | 0.023 | 0.163 | 0.156 | 0.040 | 0.147 | 0.129 |
| 116 h | 0.002 | 0.152 | 0.154 | 0.015 | 0.129 | 0.119 |
| 332 h | 0.000 | 0.149 | 0.149 | 0.003 | 0.085 | 0.091 |
| (40° C.) 20 h | 0.001 | 0.157 | 0.154 | 0.004 | 0.107 | 0.073 |
| 44 h | 0.000 | 0.150 | 0.144 | 0.002 | 0.080 | 0.037 |
| 116 h | | 0.137 | 0.124 | | 0.002 | 0.019 |
| 332 h | | 0.106 | 0.097 | | 0.000 | 0.017 |
| 524 h | | 0.091 | 0.082 | | | 0.016 |

TABLE 5-4

Blank Correction Value

| Storage Period | Enzyme Solution (s) | (t) | (u) |
|---|---|---|---|
| (10° C.) | | | |
| 20 h | 0.172 | 0.181 | 0.172 |
| 44 h | 0.168 | 0.180 | 0.167 |
| 116 h | 0.165 | 0.177 | 0.164 |
| 332 h | 0.155 | 0.175 | 0.156 |
| 524 h | 0.149 | 0.175 | 0.153 |
| (25° C.) | | | |
| 20 h | 0.149 | 0.179 | 0.157 |
| 44 h | 0.133 | 0.175 | 0.144 |
| 116 h | 0.099 | 0.171 | 0.114 |
| 332 h | 0.056 | 0.163 | 0.068 |
| (40° C.) | | | |
| 20 h | 0.026 | 0.162 | 0.039 |
| 44 h | 0.014 | 0.150 | 0.021 |
| 116 h | 0.005 | 0.118 | 0.009 |
| 332 h | 0.002 | 0.066 | 0.002 |
| 524 h | | 0.049 | |

TABLE 6-1

Relative Value

| Storage Period | Blank (0) | Enzyme Solution (a) | (b) | (c) | (d) | (e) |
|---|---|---|---|---|---|---|
| (10° C.) 20 h | | 100.0 | 100.0 | 100.0 | 100.0 | 100.0 |
| 44 h | | 97.4 | 91.1 | 95.2 | 94.8 | 99.3 |
| 116 h | | 95.7 | 77.2 | 96.2 | 92.9 | 93.7 |
| 332 h | | 96.8 | 41.7 | 92.9 | 91.9 | 91.1 |
| 524 h | | 93.5 | 28.2 | 91.5 | 91.0 | 90.0 |
| (25° C.) 20 h | | 101.7 | 37.5 | 96.2 | 96.7 | 90.9 |
| 44 h | | 97.2 | 13.9 | 90.9 | 96.2 | 87.0 |
| 116 h | | 90.8 | 3.5 | 93.1 | 91.6 | 73.5 |
| 332 h | | 77.4 | 0.0 | 85.9 | 82.9 | 46.2 |
| (40° C.) 20 h | | 96.8 | 0.0 | 92.9 | 92.7 | 37.1 |
| 44 h | | 91.0 | 0.0 | 86.7 | 87.7 | 23.0 |
| 116 h | | 78.9 | | 77.6 | 76.4 | 10.0 |
| 332 h | | 57.2 | | 58.5 | 55.1 | 3.5 |
| 524 h | | 14.6 | | 47.8 | 44.1 | |
| Evaluation | | ○ | X | ◎ | ◎ | X |

TABLE 6-2

Relative Value

| Storage Period | Enzyme Solution (f) | (g) | (h) | (i) | (j) | (k) |
|---|---|---|---|---|---|---|
| (10° C.) 20 h | 100.0 | 100.0 | 100.0 | 100.0 | 100.0 | 100.0 |
| 44 h | 81.2 | 74.9 | 97.7 | 96.7 | 98.8 | 98.2 |
| 116 h | 76.4 | 42.6 | 96.0 | 94.5 | 97.2 | 98.2 |
| 332 h | 46.4 | 14.2 | 93.1 | 74.7 | 87.0 | 96.5 |
| 524 h | 43.5 | 9.3 | 91.2 | 59.2 | 83.0 | 95.6 |
| (25° C.) 20 h | 60.1 | 15.8 | 95.2 | 98.0 | 85.6 | 98.0 |
| 44 h | 39.9 | 4.9 | 93.3 | 94.1 | 75.1 | 97.2 |
| 116 h | 16.3 | 2.2 | 90.5 | 73.1 | 53.8 | 94.3 |
| 332 h | 5.4 | 0.0 | 85.1 | 26.1 | 27.4 | 87.4 |
| (40° C.) 20 h | 6.5 | 0.0 | 86.6 | 82.9 | 14.8 | 91.9 |
| 44 h | 2.5 | 0.0 | 76.7 | 68.2 | 7.7 | 84.7 |
| 116 h | 0.0 | | 55.9 | 22.9 | 2.6 | 69.9 |
| 332 h | 0.0 | | 29.8 | 0.4 | 1.2 | 42.3 |
| 524 h | | | 20.6 | | | 30.9 |
| Evaluation | X | X | ○ | △ | X | ◎ |

TABLE 6-3

| | Relative Value | | | | | |
|---|---|---|---|---|---|---|
| | Enzyme Solution | | | | | |
| Storage Period | (l) | (m) | (n) | (o) | (p) | (q) |
| (10° C.) 20 h | 100.0 | 100.0 | 100.0 | 100.0 | 100.0 | 100.0 |
| 44 h | 96.3 | 95.0 | 96.5 | 97.7 | 93.0 | 98.3 |
| 116 h | 98.5 | 79.1 | 95.7 | 96.3 | 77.0 | 95.5 |
| 332 h | 96.5 | 55.4 | 94.6 | 95.9 | 59.3 | 94.8 |
| 524 h | 54.8 | 37.8 | 91.4 | 94.0 | 52.9 | 91.4 |
| (25° C.) 20 h | 96.5 | 53.6 | 97.5 | 97.3 | 61.3 | 96.6 |
| 44 h | 95.2 | 24.8 | 94.9 | 96.7 | 35.2 | 94.6 |
| 116 h | 94.6 | 2.2 | 88.5 | 95.5 | 13.1 | 82.8 |
| 332 h | 64.7 | 0.0 | 87.0 | 92.4 | 2.6 | 54.5 |
| (40° C.) 20 h | 91.1 | 0.7 | 91.6 | 95.5 | 3.5 | 68.9 |
| 44 h | 82.8 | 0.0 | 87.4 | 89.5 | 1.7 | 51.3 |
| 116 h | 61.0 | | 80.0 | 77.1 | | 1.3 |
| 332 h | 10.8 | | 61.9 | 60.1 | | 0.2 |
| 524 h | 7.5 | | 53.3 | 50.8 | | |
| Evaluation | ○ | X | ◎ | ◎ | X | Δ |

TABLE 6-4

| | Relative Value | | | |
|---|---|---|---|---|
| | Enzyme Solution | | | |
| Storage Period | (r) | (s) | (t) | (u) |
| (10° C.) | | | | |
| 20 h | 100.0 | 100.0 | 100.0 | 100.0 |
| 44 h | 99.3 | 97.7 | 99.1 | 97.5 |
| 116 h | 88.3 | 95.9 | 97.8 | 95.5 |
| 332 h | 97.6 | 90.3 | 96.7 | 90.7 |
| 524 h | 94.8 | 86.4 | 96.7 | 88.9 |
| (25° C.) | | | | |
| 20 h | 95.2 | 86.6 | 98.9 | 91.3 |
| 44 h | 92.1 | 77.1 | 96.7 | 83.7 |
| 116 h | 85.2 | 57.6 | 94.3 | 66.4 |
| 332 h | 65.2 | 32.6 | 89.9 | 39.6 |
| (40° C.) | | | | |
| 20 h | 52.4 | 15.3 | 89.2 | 22.9 |
| 44 h | 26.4 | 8.3 | 82.7 | 12.4 |
| 116 h | 13.6 | 3.1 | 64.9 | 5.0 |
| 332 h | 12.1 | 1.0 | 36.6 | 1.4 |
| 524 h | 11.4 | | 27.0 | |
| Evaluation | ○ | x | ◎ | Δ |

According to the results shown in above Tables, in the enzyme solutions containing calcium ions or manganese ions, trypsin was excellently stabilized, and improvement in the enzymatic activity was also observed. On the other hand, in the enzyme solution not containing any ions and in the enzyme solution containing zinc ions, the enzymatic activity was quickly decreased under a storage condition at 40° C., and moreover, the enzymatic activity was also decreased under a storage condition at 10° C. Accordingly, even though zinc ions are also divalent cations, they do not have an effect to stabilize trypsin as well as an effect to improve the enzymatic activity. Furthermore, in the enzyme solution containing magnesium ions, the stability of trypsin was also quickly decreased. Furthermore, the higher the buffer concentration, the better the stability of trypsin. Also, considering the relationship between the pKa and the pH of the buffer solution, it was confirmed that the stability and the enzymatic activity of trypsin were further improved when the pKa was higher than the pH.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A method of stabilizing trypsin before reaction of the trypsin with a substrate, comprising dissolving trypsin in a buffer solution having a pH at which trypsin is active, wherein the pKa of the buffer solution is higher than the pH of the buffer solution and further comprising calcium and manganese ions, whereby a stabilized trypsin solution is formed.

2. The method according to claim 1, wherein the total concentration of calcium and manganese ions in the buffer solution is in a range of 1 to 200 mmol/l.

3. The method according to claim 2, wherein the total concentration of calcium and manganese ions in the buffer solution is in a range of 3 to 10 mmol/l.

4. The method according to claim 1, wherein the concentration of the buffer solution is at least 10 mmol/l.

5. The method according to claim 4, wherein the concentration of the buffer solution is between 50 to 500 mmol/l.

6. The method according to claim 1, wherein the buffer solution comprises at least one buffer selected from the group consisting of glycylglycine buffer, tris buffer, N-tris(hydroxymethyl)-methyl-2-aminoethanesulfonic acid buffer, N-(2-acetamido)iminodiacetic acid buffer, triethanolamine buffer, imidazole buffer, glycine buffer, and 2-[4-(2-hydroxyethyl)-1-piperazinyl]ethanesulfonic acid buffer.

7. The method according to claim 1, wherein the buffer solution has a pH of between 5 and 10.

8. The method according to claim 7, wherein the buffer solution has a pH of between 6.5 and 8.5.

9. A stabilized trypsin solution, comprising trypsin and a buffer solution having a pH at which trypsin is active, wherein the pKa of the buffer solution is higher than the pH of the buffer solution, the buffer solution comprising calcium and manganese ions.

10. A method for measuring enzymatic activity of trypsin, which comprises:
  (a) dissolving trypsin in a buffer solution having a pH at which trypsin is active, wherein the pKa of the buffer solution is higher than the pH of the buffer solution, and comprising calcium and manganese ions whereby a stabilized trypsin solution is formed;
  (b) adding a substrate for trypsin to the stabilized trypsin solution; and
  (c) measuring the activity of the trypsin.

11. The method according to claim 10, wherein the substrate comprises at least one selected from the group consisting of α-benzoyl-arginine-p-nitroanilide, Nα-p-tosyl-L-arginine methyl ester, and Nα-p-benzoyl-L-arginine ethyl ester.

12. A method of storing trypsin, comprising dissolving trypsin in a buffer having a pH at which trypsin is active, wherein the pKa of the buffer solution is higher than the pH of the buffer solution, and comprising calcium and manganese ions, to form a stabilized trypsin solution, and storing the stabilized solution for later reaction with a substrate.

13. The method according to claim 12, wherein the total concentration of calcium and manganese ions in the stabilized trypsin solution is in a range of 1 to 200 mmol/l.

14. The method according to claim 12, wherein the total concentration of calcium and manganese ions in the stabilized trypsin solution is in a range of 3 to 10 mmol/l.

15. The method according to claim 12, wherein the concentration of the buffer is at least 10 mmol/l.

16. The method according to claim 12, wherein the concentration of the buffer is between 50 to 500 mmol/l.

17. The method according to claim 12, wherein the stabilized trypsin solution comprises at least one buffer selected from the group consisting of glyciglycine buffer, tris buffer, N-tris(hydroxymethyl)-methyl-2-aminoethanesulfonic acid buffer, N-(2-acetamido) iminodiacetic acid buffer, triethanolamine buffer, imidazole buffer, glycine buffer, and 2-[4-(2-hydroxyethyl)-1-piperazinyl]ethanesulfonic acid buffer.

18. The method according to claim 12, wherein the stabilized trypsin solution has a pH of between 5 and 10.

19. The method according to claim 12, wherein the stabilized trypsin solution has a pH of between 6.5 and 8.5.

* * * * *